United States Patent
Ihde

(10) Patent No.: US 6,991,463 B2
(45) Date of Patent: Jan. 31, 2006

(54) DENTAL IMPLANT AND METHOD OF INSERTION

(75) Inventor: Stefan Ihde, Linderstr. 68, CH-8738 Uetliburg (CH)

(73) Assignee: Stefan Ihde, Uetiburg (CH)

( * ) Notice: Subject to any disclaimer, the term of this patent is extended or adjusted under 35 U.S.C. 154(b) by 290 days.

(21) Appl. No.: 10/163,034

(22) Filed: Jun. 5, 2002

(65) Prior Publication Data

US 2003/0003419 A1 Jan. 2, 2003

Related U.S. Application Data

(63) Continuation-in-part of application No. 09/829,351, filed on Apr. 9, 2001, now Pat. No. 6,402,516, which is a continuation of application No. 09/437,643, filed on Nov. 10, 1999, now abandoned.

(30) Foreign Application Priority Data

| Nov. 11, 1998 | (DE) | ................................... 298 20 487 U |
| May 4, 1999 | (DE) | ................................... 299 08 207 U |
| Aug. 25, 1999 | (EP) | ........................................ 99250289 |
| Feb. 14, 2002 | (DE) | ................................... 202 02 424 U |

(51) Int. Cl.
*A61C 8/00* (2006.01)

(52) U.S. Cl. ...................................................... 433/176
(58) Field of Classification Search ................ 433/176, 433/174, 173, 172
See application file for complete search history.

(56) References Cited

U.S. PATENT DOCUMENTS 3,465,441 A * 9/1969 Linkow ....................... 433/176
3,925,892 A 12/1975 Juillet (Continued)

FOREIGN PATENT DOCUMENTS

| DE | 298 12 642 | 7/1998 |
| EP | 0 214 962 | 6/1990 |

(Continued)

*Primary Examiner*—Melba Bumgarner
(74) *Attorney, Agent, or Firm*—Husch & Eppenberger, LLC; Robert C. Haldiman

(57) ABSTRACT

A one-piece dental implant for endosteal and combined endosteal/subperiosteal osseointegration includes a force-transferring foot part for insertion into a jaw, the foot part including a frame in a closed geometric form having an interior open area and at least one bar connected with the frame and extending into the interior open area of the geometric form, said geometric form including at least a partial ring shape; a post that projects out of the jaw, said post connected with the foot part through the bar; and wherein a profile of the bar has a first height at a first transition region where it connects with the closed frame and a second height, which is greater than the first height, at a second transition region where it connects with the post, the height of the bar tapering from the second height to the first height.

A method of inserting the disclosed one-piece dental implant for endosteal and combined endosteal/subperiosteal osseointegration into an alveolar bone with a vestibular side and a palatal side includes the steps of providing a one-piece dental implant having a force-transferring foot part for insertion into the alveolar bone and a post that projects out of the alveolar bone; inserting the dental implant into the vestibular side of the alveolar bone; securely engaging the dental implant in the palatal side of the alveolar bone, leaving a part of the dental implant protruding from the vestibular side of the alveolar bone; bending and adapting the protruding part of the dental implant to the vestibular side of the alveolar bone; and trimming extraneous parts of the dental implant.

31 Claims, 6 Drawing Sheets

U.S. PATENT DOCUMENTS

| | | |
|---|---|---|
| 4,187,609 A | 2/1980 | Edelman |
| 4,344,757 A | 8/1982 | Streel |
| 4,722,687 A | 2/1988 | Scortecci |
| 4,768,956 A | 9/1988 | Kurpis |
| 4,815,974 A | 3/1989 | Scortecci |
| 4,964,801 A | 10/1990 | Kawahara et al. |
| 5,312,255 A | 5/1994 | Bauer |
| 5,344,457 A | 9/1994 | Pilliar et al. |
| 5,571,017 A | 11/1996 | Niznick |
| 5,989,030 A * | 11/1999 | Suga .......................... 433/176 |

FOREIGN PATENT DOCUMENTS

| | | |
|---|---|---|
| EP | 0 388 576 | 9/1990 |
| EP | 0 935 949 | 8/1999 |
| FR | 2 302 715 | 10/1976 |
| FR | 75 07078 | 10/1976 |

* cited by examiner

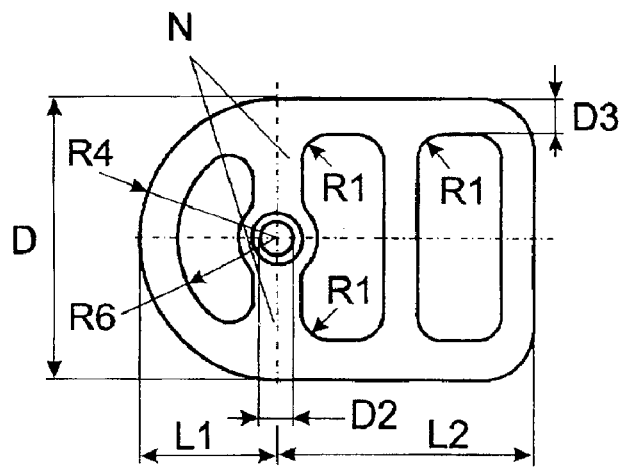
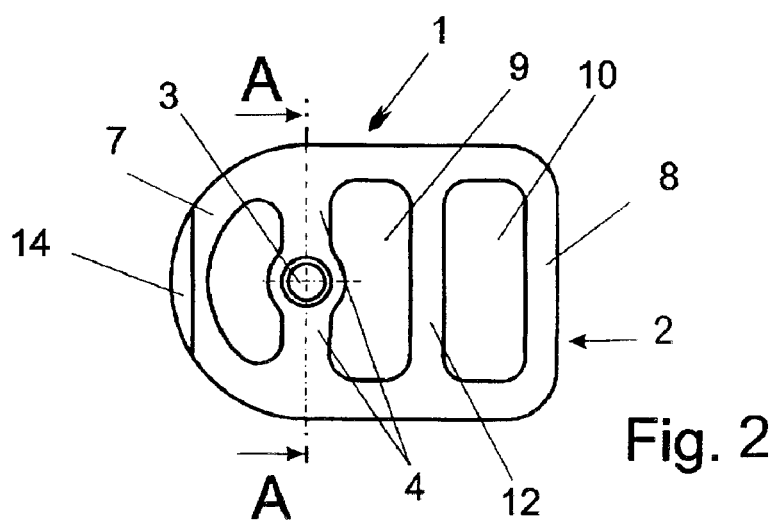

DENTAL IMPLANT AND METHOD OF INSERTION

CROSS REFERENCE TO RELATED APPLICATIONS

This application is a continuation-in-part of U.S. application Ser. No. 09/829,351 filed Apr. 9, 2001, now U.S. Pat. No. 6,402,516, which is a continuation of U.S. application Ser. No. 09/437,643 filed Nov. 10, 1999, now abandoned, which claimed priority of German Application No. 298 20 487.8 filed on Nov. 11, 1998, German Application No. 299 08 207.5 filed on May 4, 1999, and European Application No. 99 250 289.8 filed on Aug. 25, 1999. This application also claims priority of German Application No. 202 02 424.5 filed on Feb. 14, 2002.

TECHNICAL FIELD OF THE INVENTION

The invention relates generally to dental prosthetics and, more particularly, to a dental implant for endosteal and combined endosteal/subperiosteal basal osseointegration and to a method of inserting such an implant.

DESCRIPTION OF THE RELATED ART

Dental screw, blade, and cylinder implants which osseointegrate along the vertical axis of the implant are already known. Basally osseointegrated implants developed from box and disk forms. For instance, U.S. Pat. No. 3,925,892 (Juillet) describes an implant having a rectangular base part and a post screwed into the base part. A one-piece implant with a separate abutment and a thread on the vertical portion of the implant is known from FR 2,302,715 (Clune-Cost). According to U.S. Pat. No. 4,722,687, Scortecci later developed a cutter as an osteotomy instrument for such an implant type, or an implant which serves as its own insertion instrument (U.S. Pat. No. 4,815,974). Symmetrically designed lateral implants as described in U.S. Pat. No. 4,344,757 (Streel) are less important, as is the development described in U.S. Pat. No. 4,964,801 (Kawahara), which offers an interrupted, preferably perforated, surface of a base part designed as a disk.

Because of the limited number of implants per jaw, special requirements are increasingly being placed on the material and design of the implants to be used. These requirements include:

that the properties of the implant material be as similar as possible to those of the bone, with corrosion resistance and biocompatibility;

that the mechanical strength of the implant be very high with the smallest possible implant dimensions, the small dimensions being necessary to attain good defense against infection by good blood supply, and to give the smallest possible uninterrupted implant surface;

that the forces applied be distributed evenly to the cortical bone of the jaw;

that there be no force transfer directly to the jaw bone through the vertical part of the implant; and that the range of different implant sizes, which must be stocked, be as small as possible.

It is advantageous to transfer the masticatory forces into bone areas which are farther away from the post. In addition, the elastic properties of the implant should match the elasticity of the part of the facial skeleton treated with this implant. At the same time, though, the forces increase in the vicinity of the horizontal implant part, especially in the vicinity of the post. Increasing leverage produces this increase in force. In very unfavorable cases, this can cause fractures and breaks in the implant due to peak stresses, especially in the base part.

The present invention is directed to overcoming one or more of the problems set forth above.

SUMMARY OF THE INVENTION

An aspect of the present invention is to provide a dental implant having implant geometry which allows rapid, low-stress isoelastic integration of the implant into the jaw bone while assuring that the basally osseointegrated implant is highly resistant to fatigue and breakage.

In accordance with an aspect of the invention, there is provided a one-piece dental implant for endosteal and combined endosteal/subperiosteal osseointegration that includes a force-transferring foot part for insertion into a jaw, the foot part including a frame in a closed geometric form having an interior open area and at least one bar connected with the frame and extending into the interior open area of the geometric form, said geometric form including at least a partial ring shape; a post that projects out of the jaw, said post connected with the foot part through the bar; and wherein a profile of the bar has a first height at a first transition region where it connects with the closed frame and a second height, which is greater than the first height, at a second transition region where it connects with the post, the height of the bar tapering from the second height to the first height.

A method of inserting a one-piece dental implant for endosteal and combined endosteal/subperiosteal osseointegration into an alveolar bone with a vestibular side and a palatal side includes the steps of providing a one-piece dental implant having a force-transferring foot part for insertion into the alveolar bone and a post that projects out of the alveolar bone; inserting the dental implant into the vestibular side of the alveolar bone; securely engaging the dental implant in the palatal side of the alveolar bone, leaving a part of the dental implant protruding from the vestibular side of the alveolar bone; bending and adapting the protruding part of the dental implant to the vestibular side of the alveolar bone; or trimming extraneous parts of the dental implant.

While crestal implants, i.e., screws and cylinder implants, are made rigid by the manufacturer according to the specifications, and so, together with the bridges mounted on them, give rigid implant prosthetic systems, the one-piece, basally osseointegrated implants according to an embodiment of the present invention make possible an approximately isoelastic connection between the compact jaw bone and the denture. Thus the bending forces that arise are better accepted because of the geometry of the base part and are distributed more evenly over the whole base part with lower peak stresses.

It has been found that the assumption that the implant must be rigid and fixed in the bone to prevent osteolysis is not correct. If the implant is in a region of bone subject to functional flexion, then the load transferring surfaces of the implant must follow that movement to remain attached to the bone on all sides.

Because of the implant geometry described, it is also possible to provide approximately isoelastic connections between bone and implant, in which the bone adapts to the elasticity of the implant by altering the matrix, changing the degree of mineralization and enlarging load transferring areas by bone induction. That happens extraordinarily successfully with the implant described.

The implant geometry described and the implants produced using it allow an isoelastic bond to the compact and spongy jaw bones. That avoids both force peaks with osteolytic effect and excessive movement of the implant with the potential consequences of osteolyses due to mobility, and inflammation of the connective tissue. That, though, requires a special distribution of stress from the forces being absorbed by the implant and transferred to the jaw in the vicinity of the framework, of the post, of the transition between the post and the framework, and in the transition to the abutment or bridge.

These aspects are merely illustrative of the innumerable aspects associated with the present invention and should not be deemed as limiting in any manner. These and other aspects, features and advantages of the present invention will become apparent from the following detailed description when taken in conjunction with the drawings.

BRIEF DESCRIPTION OF THE DRAWINGS

Reference is now made more particularly to the drawings which illustrate the best presently known mode of carrying out the invention and wherein similar reference characters indicate the same parts throughout the views.

FIG. 1 is a plan view of a one-piece, basally osseointegratable dental implant showing various geometric relationships.

FIG. 2 is a plan view of a one-piece, basally osseointegratable dental implant similar to FIG. 1.

FIG. 3 is a partial sectional view of the dental implant of FIG. 2 taken generally along line A—A.

FIG. 4 is a side view of the dental implant of FIG. 2.

DETAILED DESCRIPTION

Figure 5:
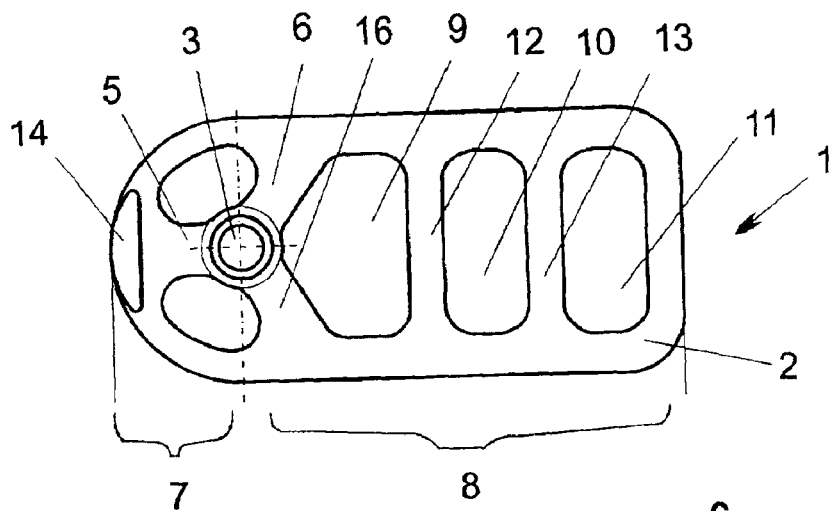
FIG. 5 is a plan view of a one-piece, basally osseointegratable dental implant with a variable-sized foot part according to one embodiment.

The first truly basally osseointegrated implants have been proposed in EP 0 935 949 A1, the disclosure of which is hereby incorporated by reference. They are different from implants, which either have a totally rigid design or transfer forces through expanded surfaces along the vertical post (e.g., FR 2,302,715). On the basis of these basally osseointegrated implants, it is possible to provide strategic implant positioning independently of the presence of a vertical bone supply and to provide basally osseointegrated implant prosthetic systems. For example, the annular design of the base part and the connection of the base part to the post through bars has the advantage that, if high forces are applied, the post can deflect slightly into the spongiosa, while the annular base remains solidly anchored in the compacta, supporting a lasting solid seating of the implant in the jaw bone. Further, the positioning of the post outside the center of the base part, in the center of the semicircular ring, as well as the placement of the bars, preferably in the transition region between the semicircular ring and the rectangular outer frame of the base part not only allow acceptance and transfer of greater forces but, in particular, provide matching of the implant being used to the anatomy of the jaw bone and to the implant bed which is prepared surgically by milling.

The basally osseointegratable implant 1 shown in the figures comprises a base part 2, which is inserted into an implant bed prepared surgically, by milling into the jaw bone, and a post 3, on which a crown or some other type of dental prosthesis is mounted after the implant has healed. The post 3 is connected to the outer frame 8 of the base part by bars N, 4, 5, 6 and 16. Bars N, 4, 5, 6 and 16 join the profile of the outer frame 8, with the thickness H3, D3, through radii R1. As shown in FIG. 4, advantageously the height of a surface increase 17 to the free smooth part of the post or shaft 3, amounts to at least half of the height of the post 3 to an external thread 19 for securing an abutment or the like. Particularly good load distribution is attained if the profile of the transition from the post to the bars has two radii, an upper radius R3 and a lower radius R2. However, a good dynamic result is also attained if there is only one radius R5, though it must include an angle of more than 90 degrees. As can be seen from FIG. 3, the bars N, 4, 5, 6 and 16 of implant 1 as described in the invention are thicker in the vicinity of the foot of the post 3, with thickness H1. That thickness diminishes to the thickness H3; D3 of the outer frame 8 or the semicircular ring 7 toward the outer frame 8 and the semicircular ring 7 of the base part 2.

The bars N, 4, 5, 6 and 16 of implant 1 may have a round profile cross section, or an oval profile cross section.

Depending on the forces to be introduced into implant 1 and the hardness of the selected implant material, the design of the implant, for a given diameter D of post 3, is determined by the radii R1 and R3 and by the thicknesses H1 and H3.

Post 3 is itself connected to the bars N, 4, 5, 6 and 16 through radii R3 at its foot region. It has a constricted section 15, which takes on the function of a deformation zone and is the place where any breakage should occur. In one embodiment, the constricted portion 15 is about ⅓ the length of the post, with expanded surfaces 17, hereafter described in detail, below this constricted portion 15. When the bending forces are very high, deformations occur particularly in this region, protecting the base part of the implant from possible fracture. The constricted region is dimensioned, in relation to the base, so that, if peak forces occur, there will be a fracture in the vicinity of the constricted region, while the base part remains undamaged. Thus replacement of the base part can be avoided. A fracture is generally the result of a prosthetic overload, which can be corrected after repairing the implant. In case of a fracture, for example, the implant can be repaired by affixing a replacement piece to the stump of the post as by cutting a thread on the remaining stump of the post, or by welding, or otherwise adhering the replacement piece. As the constricted region is more elastic and therefore moves more, a surface expansion would result in more irritation of the bone and even inflammation, with the known bad consequences. As mentioned previously, then, there are surface expansions 17 below the constricted region 15, while the remainder of the post 3 is given a polished surface.

Careful selection of the implant material is important for the isoelastic connection to the compact and spongy jaw bone. Implants may be made from pure titanium, which is available in four degrees of hardness. The softer the implant material is, the more closely its elasticity matches that of the jaw bone and the more easily the bone grows around the inserted implant 1. For instance, if one uses titanium with a higher degree of hardness because of the forces, which must be transferred, one can compensate for the bad effect on the elasticity by appropriately dimensioning the base part 2. Harder titanium needs a larger support.

With pure, softer titanium having a tensile strength of 250–450 MPa, for example, the profile height (i.e. thickness H1) of the framework for the base part 2 should be selected relatively thin, but no less than 0.6 mm. If the thickness H1 of the framework of the base part 2 is excessive, the implant 1, or the implant material, will not be elastic enough. On the other hand, if the areas of the implant, which transfer the forces, are too small, osteolysis will occur because the load per unit area is too great. Bone damage can also occur if the uninterrupted foreign body surface introduced into the body is too large.

While soft titanium can adapt to and bond well with the bone, it is also possible to produce very elastic implants with an alloy comprising about 85 parts titanium and 15 parts of molybdenum. It is advantageous to select such an alloy if the implants must be unusually delicate. Other ratios of titanium to molybdenum give similarly good results.

At the same time, elasticity zones are produced by the radii R1 and R3 and the thicknesses H1 and H3, together with the external thread 19 and a suitable choice of material for an abutment A at the distal end of post 3. In particular, an elastic zone is formed in the region of the contact between the abutment A and the post 3. A softer material, preferably Delrin, is used instead of the titanium previously described for the abutment A. The Delrin remains stable with respect to retention of a crown cemented onto it. Each of the elasticity zones is optimized such that the implant 1 has the highest possible elasticity with simultaneous assurance of load transfer into the jaw bone. In this manner, it makes possible and helps assure isoelastic osseointegration of the implant 1 into the jaw bone. In practice, the implants 1 have a vertical transition profile determined by the radii R3 and the thicknesses H1, H3; and a horizontal transition profile formed by the radii R1. The two thicknesses are matched to each other so as to give a final three-dimensional implant profile optimized for load transfer.

The cutouts in the base part 2, indicated as cutouts 9, 10 and 11, are selected so that, on one hand, they are as large as possible to assure optimal blood supply which promotes healing of implant 1 into the jaw bone. On the other hand, bar N and crossbars 12, 13 have as nearly as possible a round and stress-free profile. In this design, the force transfer in the vicinity of the post is completely independent of the form and design of the cutouts in base part 2, while the radii R3 between post 3 and the bars N likewise do not affect the shape and design of the cutouts.

Because of the thickened region at the foot of post 3, the forces applied are taken up more reliably by foot part 2 and transferred to the compacta of the jaw bone. At the same time, the design assures that if any extremely high forces occur, post 3 can deflect easily into the spongiosa, thus acting against a potential fracture of the implant 1. Furthermore, as explained above, the design of the bars N, 4, 5, 6 and 16 improves the blood supply. That also promotes bone growth and healing of the implant 1 into the jaw bone.

Figure 11:
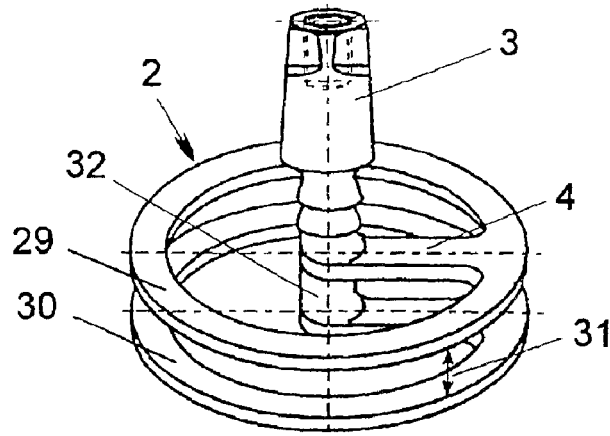
FIG. 11 is a perspective view of a one-piece, basally osseointegratable dental implant incorporating two frames of similar diameters in the foot part.

In one embodiment, base part 2 is made up of a semicircular ring 7 and a rectangular outer frame 8 which transition into each other without any discontinuity. As a deviation from that configuration, base part 2 can also have a round shape, as shown in FIG. 11, or be shaped according to the design of FIG. 7.

As is further apparent from FIGS. 1, 2 and 5, the rectangular outer frame 8 is divided into segments 9, 10 and 11, which are separated by crossbars 12, 13. The advantage of this design is that, depending on the anatomy of the jaw bone, unneeded portions of the base part 2 can easily be removed. Simply removing the unneeded segments of the base part 2 can produce any particular size of implant foot. Thus, in the dental practice, it is possible to provide extensive and simple matching of the implant 1 being inserted to the jaw anatomy of the individual patient, while simultaneously reducing the continuous availability of implants with base parts of different sizes. That makes production and storage if implants simpler and less expensive.

To promote rapid healing of the implant and to get better and more solid mounting in the jaw bone, base part 2 and the lower part of the post 3 enclosed by the compacta are given the previously mentioned surface increase 17 which enlarges the surface, while the region of the post 3 near the alveolar ridge has a smooth, preferably polished, surface. In this manner it is possible, by simple means, to counter a bacterial inflammation caused by surface enlargements, especially in the connective tissue in the vicinity of the alveolar ridge. For implants with multiple base parts arranged in the axial direction of the post 3 (see FIG. 11 hereafter described) a crestal base part 29 and the post 3 are given a smooth polished surface, and a basal base part 30 and a shaft portion 32 connecting the base parts together are given a surface enlargement which can be produced by sandblasting, etching, a combination of the two processes, or the like. That promotes healing and, in particular, improves the initial support of the base parts in the lower-lying regions of the jaw bone, which are protected from infection.

It has been found, especially for implants having numerous base parts separated from each other, that restructuring of the bone and forming of connective tissue occurs because of mechanical irritations in the vicinity of the post near the alveolar ridge and the crestal base part 29. This new structure initially includes no bacteria. Only at a later time does it become populated with bacteria so that, under some circumstances, resection of the crestal base part may become necessary. The mechanical irritations are due primarily to surface extensions that have previously been provided. Irritations can be limited to a large extent if those regions of the implant have a smooth, highly polished surface, contrary to state of the art practice.

Figure 9:
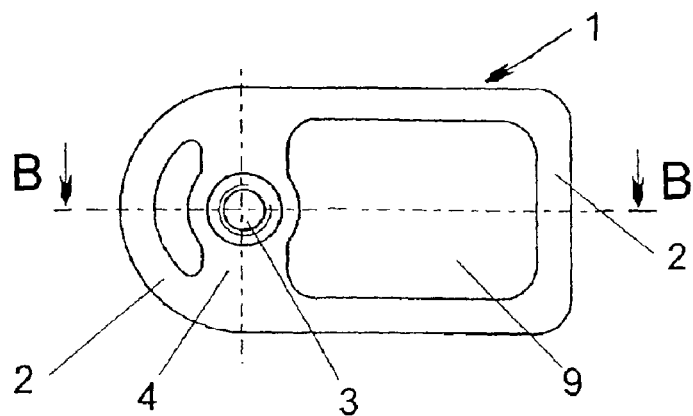
FIG. 9 is a plan view of yet another one-piece, basally osseointegratable dental implant.
Figure 10:
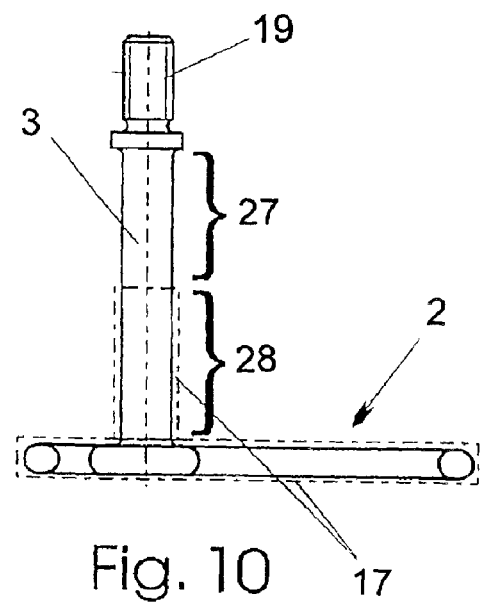
FIG. 10 is a section view of the dental implant of FIG. 9 taken along line B—B.

In the embodiment shown in FIGS. 9 and 10, the implant 1 is provided in a thread-adjacent head region 27 with a structure-free, smooth surface, while a transition region 28 of the post 3 to the base 2 is provided with the surface enlargement 17, which surface enlargement is also on the base 2. Due to the smooth surface property of the head region 27, the deposit of plaque is less likely to occur and the tissue irritations and inflammations, which are often caused by, profiled and surface-enlarged post portions are avoided. In a particularly advantageous embodiment, the ratio between the height of the foot part or base part 2 and the height of the post 3 is in the range of approximately 1:6–1:30. Thus, it is possible, to provide a good osseo integration of the basal post portion far from the region of bacterial contamination. Simultaneously, the post 3 and the bar 4 under the action of great stress can be minimally resilient in the spongiosa of the jaw bone, thereby causing in the transition region 28 an elastic bone deformation to take place. Because of the smooth post design when there is minimal resilience of the implant in the spongiosa of the jaw bone, connecting tissue irritations and inflammations are excluded and a long term reliable and complication-free fixed seating of the foot part 2 in the compacta of the upper or lower jaw is substantially guaranteed.

Figure 11A:
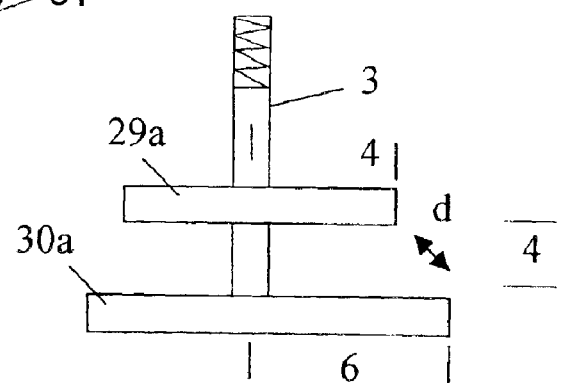
FIG. 11a is a side view of a one-piece, basally osseointegratable dental implant incorporating two frames or rings of different diameters.

The FIG. 11 embodiment is provided with two frames, 29, 30 which are located over one another and are spaced apart from one another. Together frames 29, 30 form the foot part 2 of the implant 1. In an alternate embodiment, the frames 29, 30, have different external diameters. The foot part 2 thus formed allows for a substantial adaptation of the implant to the anatomical features of the jaw and permits the full use of the bone width of the jaw. The bar 4 of the lower frame is thus located completely in the spongiosa, or soft bone region, of the jaw while the bar of the upper frame is completely received by the compacta of the bone, which is not damaged by the milling. Histological investigation has shown that the formation and orientation of secondary osteons is affected by the load transferring rings over a distance of a little more than 1.5 mm. Hence in a double disk implant with a space between the rings of 3 mm. or less, the bone forming forces on the rings are adversely influencing each other, resulting in bone formation of lesser quality in at least one of the ring's area. Relatively larger distances between the rings may be achieved also by producing an implant with significantly different ring diameters as shown in FIG. 11a. In FIG. 11a, the distance between the upper and lower rings is 4 mm, while distance d between the rings is 5 mm because the rings have significantly different diameters. In the FIG. 11a embodiment, the radius of ring 29a is 4 mm and the radius of ring 30a is 6 mm. In the FIG. 11 embodiment, frames 29, 30 are preferably spaced apart a distance 31 greater than 3 mm and are connected to one another through an additional shaft 32. Because of this greater spacing in these embodiments, which exceeds 3 mm, between the frames 29, 30, or rings 29a, 30a, the setting of the implant is improved, the hold in the upper and/or lower jaw is improved, and improved blood circulation of the interdiscal region is achieved. Moreover, the lateral stability of the implant is increased, while the basal ring frame 30 is better protected when the crestal ring frame 29 is subjected to bacterial attack. Total implant losses are virtually eliminated. Moreover, the removal of the implant or a disk of the implant is made easier. The insertion of the implant can also be performed more reliably. In particular, for brittle, cortical bones there is less danger of tearing the osteotomised interdiscal region when the ring bodies are positioned further from one another. As used herein, the terms disk, ring, frame and foot are sometimes used to describe parts having the same function.

Figure 6:
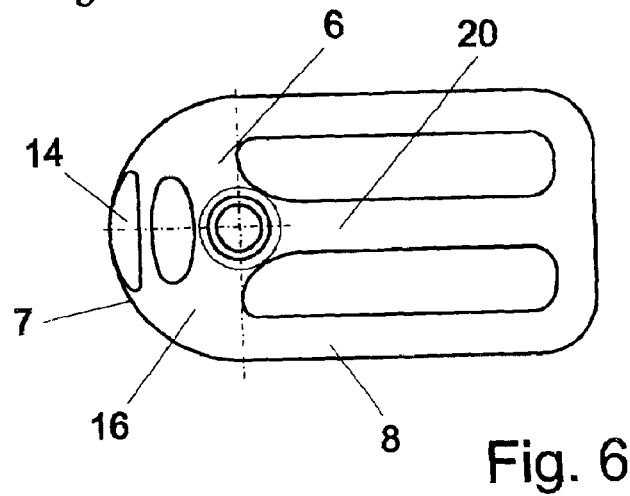
FIGS. 6 to 8 are plan views of one-piece, basally osseointegratable dental implants according to various other embodiments.

With basally osseointegrated implants having round base parts, such as shown in FIG. 11, the bars from the foot of the implant can be placed transversely, longitudinally, or obliquely with respect to the jaw bone, according to the judgment of the dentist. For implants like those in FIG. 1 having a base part with a rectangular form at one side, though, the bar positioning and the direction of insertion of the implants is established, or predetermined, by the configuration of the implant foot. The bars of previously known implants almost always end up lying parallel to the longitudinal direction of the alveolar bone. Relatively large forces must be applied to insert the implants, which are pressed into the surgical opening in the implant bed with a relatively high pressure per unit area. Those are applied, without exception, to the post, because there is practically no other part of the implant available for insertion of the implant. Those forces can cause deformations and microcracks in the posts and bars immediately on insertion. Those deformations and microcracks can later lead to breakage of the implant. This disadvantage is counteracted by placing at least one bar in the direction of implant insertion such as shown in FIGS. 5, 6 or 8. Furthermore, bar positions, altered by 120°, as in FIGS. 5, 7 or 8, result, at the same time, in a more even transfer of the forces to the outer frame of the base parts, not only during insertion of the implant, but also after healing of the implant into the jaw bone. With this bar positioning, the diameters of the individual bars can actually be reduced, in comparison with the currently known implants, and that results in further improvement of the blood supply.

With respect to the insertion of implants 1 into the implant bed, it is advantageous to have a bar arrangement in which bars 5, 6 and 16 are aligned at 120° to each other, as shown in FIGS. 5 and 8, while bar 5 or 20 is lying in the direction of insertion of the implant. This bar arrangement also gives a still better and more even distribution and transfer of the forces introduced through post 3 to base part 2 and to the jaw bone. Because post 3 is supported by the bar 5 lying in the direction of insertion, the forces due to insertion in the approximately transversely oriented bars 6 and 16 are reduced. That avoids deformations and microcracking, as can occur particularly in implants with bars 4 perpendicular to the direction of insertion. This can eventually promote breakage of the implant.

Forces applied at a right angle to bars 4 of implant 1 shown in FIGS. 1 and 4 are absorbed well by the implant because the bars 4 are relatively long and can be twisted elastically by the forces applied, which in practice act on the bar like rotational forces. Forces applied in the longitudinal axis of the bar are, on the other hand, taken up poorly. Tests have shown that the fatigue resistance of the implant decreases very seriously with such force application, and a break may occur in the bar vicinity very quickly. To avoid this problem, implants are advantageously provided with a bar arrangement as shown in FIGS. 5 to 8.

In implants with bars 6, 16 and 20 arranged as shown in FIG. 6, most of the load forces are transferred to the short side of the implant with the semicircular ring 7 of the outer frame of the base part 2, because of the asymmetric positioning of the posts 3. The forces are taken up well by the bars 6 and 16, and are transferred evenly to the jaw bone. If the post 3 is stressed by forces in the direction of the longitudinal axes of bars 6, 16, it is advantageous to use another bar 20, which lies approximately perpendicularly to those force directions, thus improving the potential for elastic deflection. In addition, the force distribution is considerably better with three bars than with two bars 4, such as shown in FIGS. 1 and 2.

However, if there should happen to be greater force introduced onto the section of base part 2 with the rectangular outer frame 8, two bars 6 and 16 should also be oriented in the direction of that segment in the interest of even force distribution, as shown in FIGS. 5 and 8.

Figure 7:
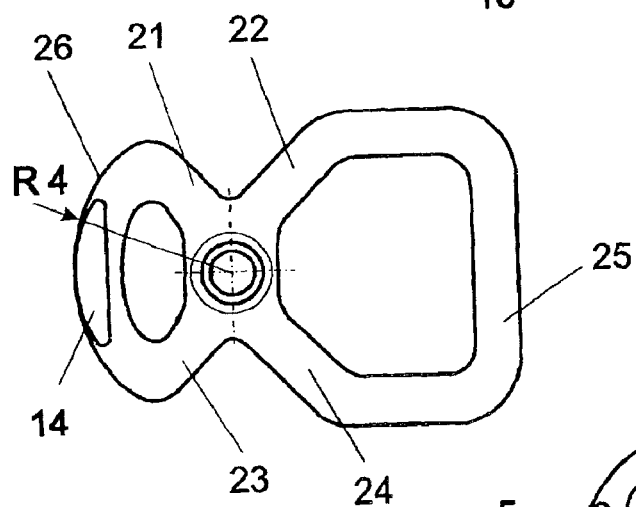
Figure 8:
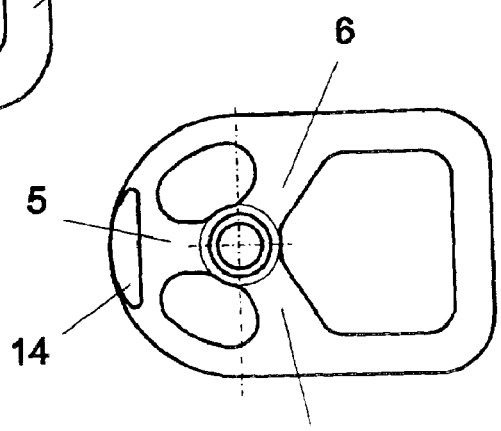

Still better force distribution is attained by a crosswise arrangement of bars 21, 22, 23 and 24, as shown in FIG. 7. In this embodiment, the previously closed outer frame 8 of base part 2 is divided into two separate outer frames, 25 and 26. The open end of each one connects to bars 22; 24 and 21; 22. Blood supply is substantially improved by the external open spaces between bars 21, 22 and 23, 24. Such a design and arrangement of the bars of the base parts results in an even better distribution of the forces introduced through the posts. In this design, the crosswise arrangement divides the outer frame of the base part into two separate segments, in which the radius R4 of the outer frame is half that of the rectangular or square outer frame on the opposite side. Due to the crosswise arrangement of the bars and the specific design of the outer frame, there are external cutouts that improve the blood supply, thus accelerating the healing process and assuring long-term immune defense.

Selection of the inner and outer radii R6 and R4 of the frame part (base part 2) can affect the deformation of the ring, which depends on the transverse loading. If the inner radius R6 is smaller than the outer radius R4, then the peak stresses occur at the nose of the rounded part and near the guide bevel. That can help to lead the peak stresses away from the vicinity of the post to the bone. According to another feature, there is a guide bevel 14 at the insertion side of base part 2, which makes insertion and positioning implant 1 in the implant bed easier.

Figure 15:
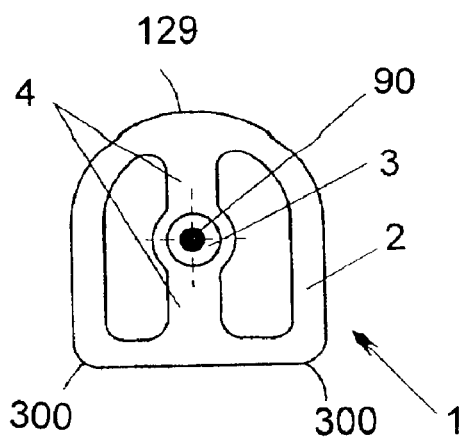
FIG. 15 is a plan view of a one-piece, basally osseointegratable dental implant showing a bar through which the foot part is connected with the shaft.

FIG. 15 shows a different foot part 2 which deviates from a square base form for a one-piece, basally osseointegratable dental implant with a different arrangement and design of the bar 4 which connects the post 3 to the foot part 2, wherein at least one body side of the base form is formed ring-shaped by a rounding 129, and the corners of the opposite side are rounded by a radii 300. The shape of the foot part 2 shown in FIG. 15 guarantees a substantial adaptation to the implant bed produced by milling and to the natural anatomy of the jaw bone with symmetrical positioning of the post to the foot part 2 center of gravity 90. As can be seen from FIG. 15, the bar 4, depending on the configuration of the foot part 2, is formed two-sided and is arranged along vertical implant axes.

Figure 12:
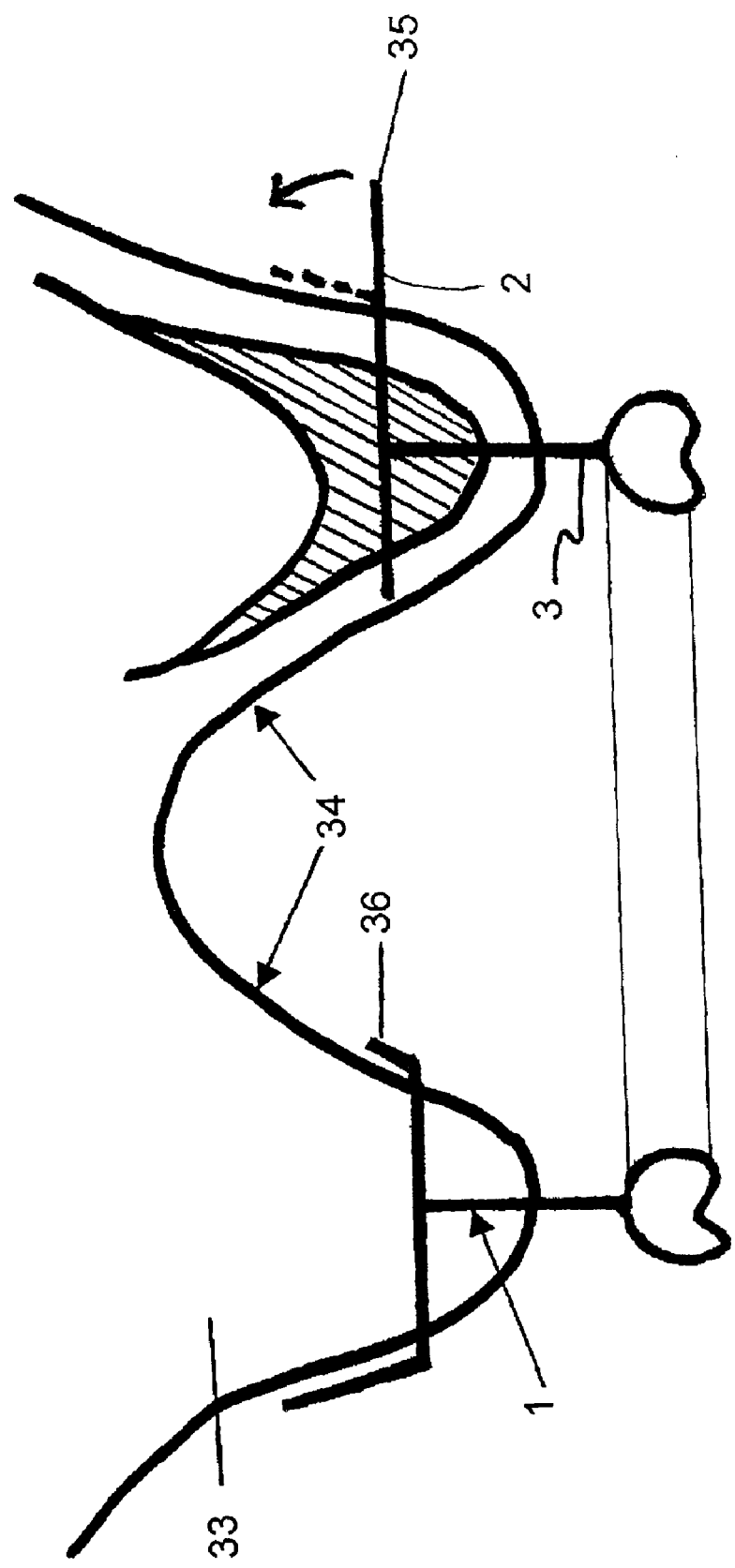
FIG. 12 is a schematic view of an insertion method for a basal osseo dental implant.

The configuration of the disclosed dental implant allows for a particularly advantageous method of insertion into the jaw illustrated in FIG. 12. First the implant 1 is inserted into the alveolar bone 33 and securely engaged in the palatal side 34 of the alveolar bone 33. At this stage the vestibular side 35 of the implant 1 protrudes out of the alveolar bone 33. Next, the protruding vestibular side 35 of the implant 1 is bent in the direction of the fona canina or the christa zygomaticaalveolaris and adapted to the form of the jaw bone. It is advantageous to ensure good cortical contact as this will reduce the necessary number of implants. In those cases in which the palatal side 36 of the implant 1 also protrudes out of the alveolar bone 33, it should also be bent and adapted to the form of the bone. The bent areas of the frame are initially in a subperiosteal position. The bent areas also secure the implant against lateral chewing forces, which is especially important during the period after insertion of the implant but prior to osseointegration. The thicker area of the implant, defined by the areas of the bars at the region of the post having greater height H1, keeps the implant centered in the insertion site and minimizes undesired movement of the implant during the process of bending the protruding portions of the implant. Any protruding parts of the implant frame that are not needed should be trimmed from the implant.

Figure 13:
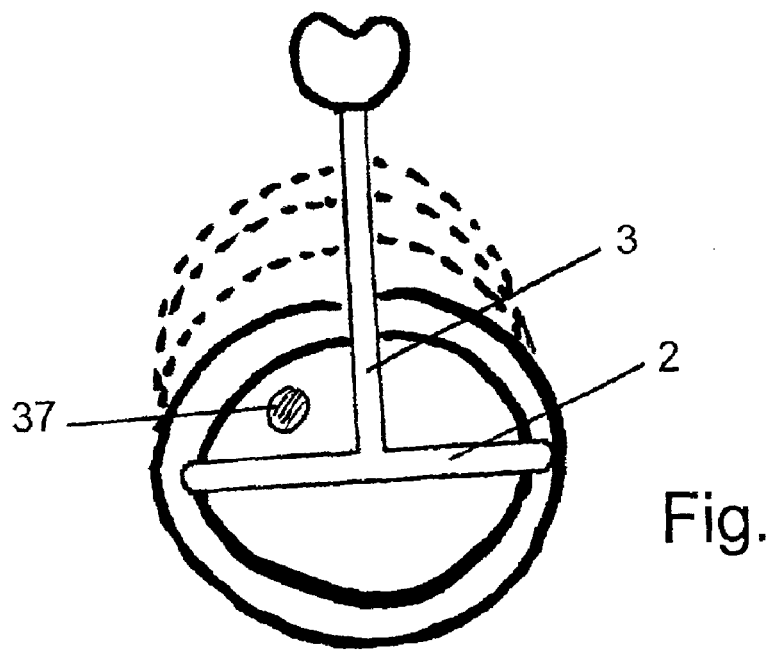
FIG. 13 is a schematic view of a preferred positioning after insertion into the jaw of a one-piece basal osseo dental implant.

As shown in FIG. 13, the proper placement of the foot part 2 is below the nerve canal 37, positioning the post 3 to one side of the nerve canal 37. The post must be made a sufficient length to account for growth of the bone while preventing the bone from coming into contact with the crown or bridge attached to the implant. As the bone continues to grow in a cranial direction, there may eventually be sufficient bone to place another implant over the nerve canal.

Using the disclosed method, it is possible to treat an entire jaw with only four implants positioned in the areas of the canines and the second molars. In cases of extraordinary atrophic mandibles, treatment with only three implants in the areas of the canines and one molar is possible. The disclosed method promotes correct functional loading of the mandible, which leads to bone growth. This bone growth may allow insertion of additional implants later.

Figure 14:
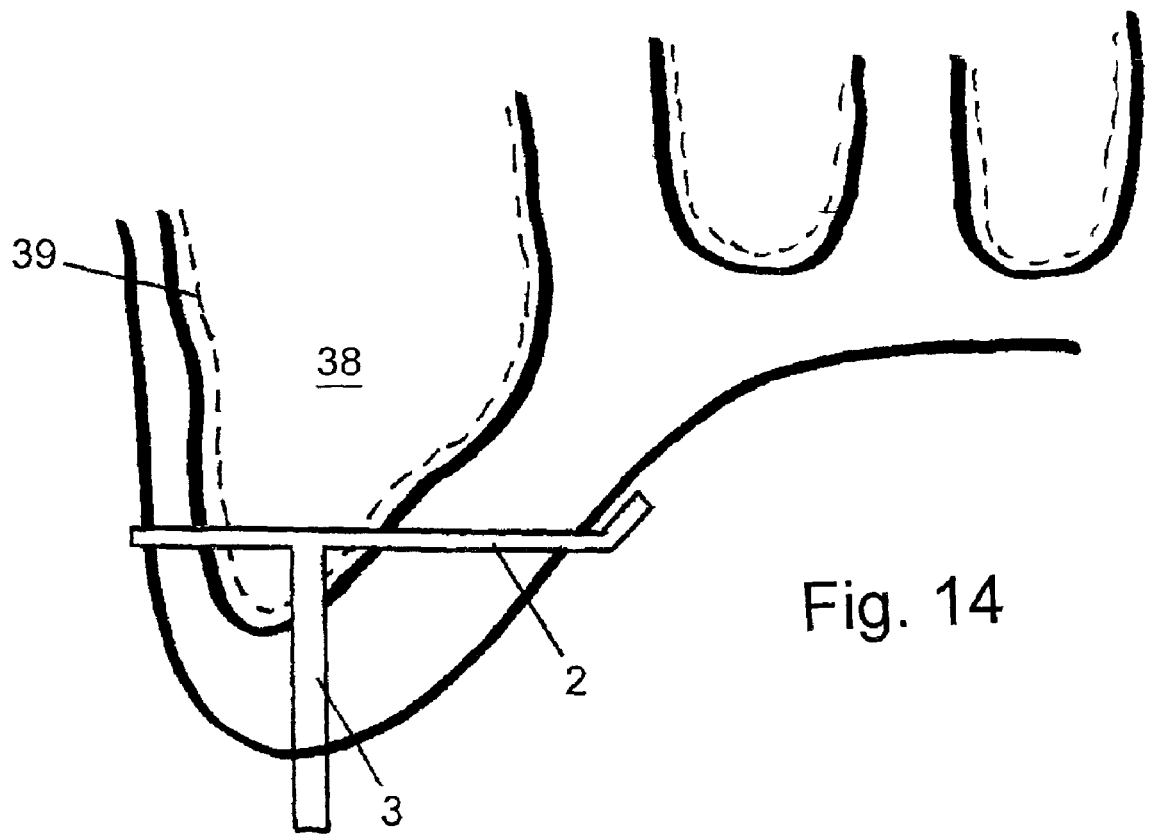
FIG. 14 is a schematic view of an insertion position in the jaw possible with a one-piece dental implant according to an embodiment of the present invention.

It is possible to insert the implant through the sinus cavity 38 into the alveolar bone as illustrated by FIG. 14. In such a procedure, the Schneiderian Membrane 39 of the sinus 38 may be damaged during the insertion procedure, but it will heal, including that portion of the membrane over the frame bars in many cases.

In summary, the method of inserting the disclosed one-piece dental implant for endosteal and combined endosteal/subperiosteal osseointegration into an alveolar bone with a vestibular side and a palatal side may include some of the following steps: providing a one-piece dental implant having a force-transferring foot part for insertion into the alveolar bone and a post that projects out of the alveolar bone; inserting the dental implant into the vestibular side of the alveolar bone; securely engaging the dental implant in the palatal side of the alveolar bone, leaving a part of the dental implant protruding from the vestibular side of the alveolar bone; bending and adapting the protruding part of the dental implant to the vestibular side of the alveolar bone; and trimming extraneous parts of the dental implant. The step of inserting the dental implant may include inserting the dental implant through the sinus cavity or inserting the dental implant with the foot part of the implant below a nerve canal in a spongiosa region of the alveolar bone and with the post at the side of the nerve canal.

Figure 16:
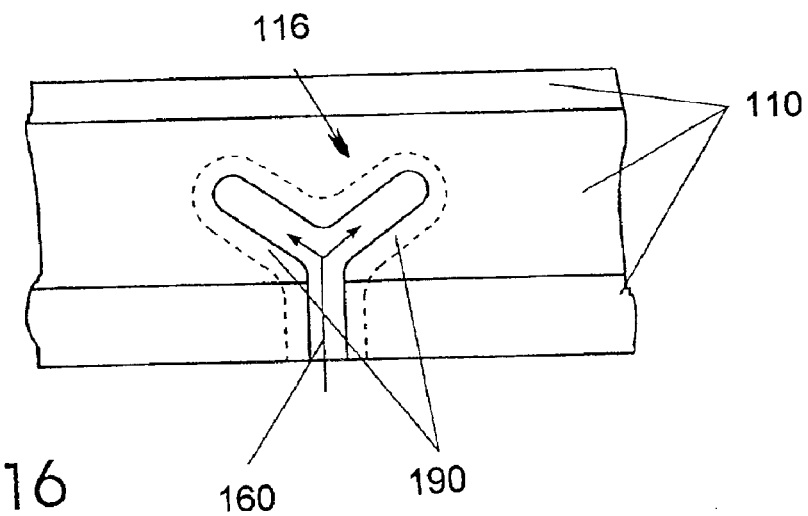
FIG. 16 is a plan view of a portion of a lower jaw with an implant bed milled into the jaw for a one-piece basal osseo dental implant according to an embodiment.
Figure 17:
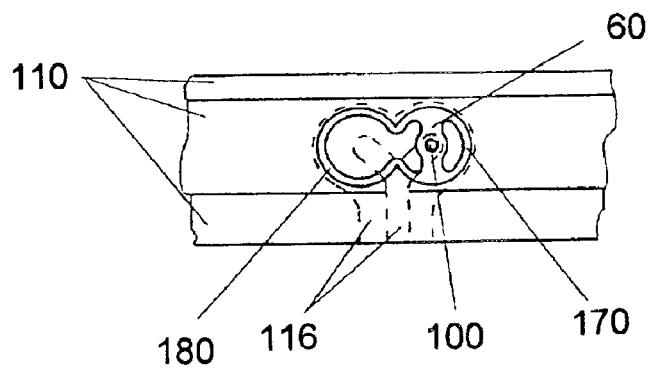
FIG. 17 is a plan view of the lower jaw portion of FIG. 17 with a one-piece basal osseo dental implant inserted into the implant bed.

FIGS. 16 and 17 illustrate a preferred embodiment of a method for inserting a one-piece basal osseo dental implant into a jaw 110. The jaw 110 includes spongiosa 112 and compacta 114 portions. In the method, an implant bed 116 is milled through the compacta 114 and into the spongiosa 112 on one side of the jaw 110 by known means. A single lateral cut 160 is made through the compacta 114. However, once the cutting tool has entered the spongiosa portion 112, two separate cuts 190 are made at angles from the single cut 160 and away from one another, forming a Y-shaped implant bed 116 in the jaw 110. A first end 170 of a one-piece dental implant 60 having a post 100 is inserted through the single lateral cut 160 and into one of the separate cuts 190. After end 170 has been inserted entirely into one of the separate cuts 190, the implant 60 is rotated in the jaw 110 to introduce a second end 180 of the implant 60 into the other separate cut 190, thereby completing insertion.

In the alternative slightly differently shaped cuts are contemplated. For example, a single longer cut 190 can be milled at about a right angle to cut 160 so that the combination of cut 160 and 190 is generally J-shaped; or the two cuts 190 may be substantially aligned so that the combination of cut 160 and cuts 190 is generally T-shaped. Such shaped cuts are especially adaptable for use with implants with an elongate foot or base part 2 such as shown in FIGS. 5, 6 or 9, for example. The procedure includes milling an implant bed into the alveolar bone by making the straight cut 160 into one side of and generally perpendicular to the alveolar bone then making the first (and possibly a second) diverging cut 190 further into the alveolar bone at an obtuse or right angle from the straight cut. The shorter end of a dental implant 1 having an elongate base part 2 is then inserted into cut 160 and into the diverging cut 190. The dental implant is then moved along the diverging cut 190 and rotated so that the opposite end thereof is placed into the cut 190.

Other objects, features and advantages will be apparent to those skilled in the art. The invention in its broader aspects is not limited to the specific steps and embodiments shown and described but departures may be made therefrom within the scope of the appended claims without departing from the principles of the invention and without sacrificing its chief advantages.

What is claimed is:

1. A one-piece dental implant adapted for endosteal and combined endosteal/subperiosteal osseointegration in a jaw, including:
   a force-transferring foot part for insertion into a jaw, the foot part including a frame in a closed geometric form having an interior open area and at least one bar connected with the frame and extending into the interior open area of the geometric form, said geometric form including at least a partial ring shape;
   said frame, said closed geometric form, said interior open area and said bar all being substantially on a single plane;
   a post adapted to project out of the jaw, said post connected with the foot part through the bar said cost being substantially orthogonal to said plane; and
   wherein a profile of the bar has a first height at a first transition region where said bar connects with the closed geometric form and a second height, which is greater than the first height, at a second transition region where said bar connects with the post, the height of the bar tapering from the second height to the first height.

2. A dental implant according to claim 1, wherein a geometric configuration of the closed geometric form, the bar, the post, the first and second transition regions, and a first and second transition radii are optimized by a computer aided optimization method.

3. A one-piece dental implant according to claim 1, further including a plurality of bars wherein the connection of each bar with the closed geometric form includes a separate transition radius.

4. A one-piece dental implant according to claim 3, wherein the closed geometric form includes a rectangular shape, said rectangular shape having a longitudinal axis, and wherein the at least one bar is oriented along the longitudinal axis.

5. A one-piece dental implant according to claim 1, further including:
   an intermediate area of the post;
   a top end of the post opposite of the foot part, said top end having a threaded area;
   an abutment connected with the threaded area; and
   elasticity zones defined by the first and second transition regions, the threaded area, the abutment, and the intermediate area of the post.

6. A one-piece dental implant according to claim 5, wherein a further elasticity zone is defined by a transition from the threaded area to the abutment, the abutment being made of a suitable abutment material.

7. A one-piece dental implant according to claim 5, wherein the threaded area includes an external screw thread and the abutment includes an internal screw thread and wherein the abutment is made of a plastic material.

8. A one-piece dental implant according to claim 7, wherein the plastic material is acetal polyoxymethylene.

9. A one-piece dental implant according to claim 1, further including a plurality of bars and wherein the bars are oriented at an angle of approximately 120° to each other.

10. A one-piece dental implant according to claim 1, further including an insertion direction defined by the direction in which the dental implant is inserted into the jaw and wherein the at least one bar is oriented in the insertion direction.

11. A one-piece dental implant according to claim 1, wherein the closed geometric form includes a rectangular shape and wherein the rectangular shape connects with the partial ring shape at first and second joints to form the closed geometric form and wherein the bar extends from an area of the first joint to an area of the second joint.

12. A one-piece dental implant according to claim 1, wherein the post includes constricted zone whereby the post will break at the constricted region when exposed to excessive force.

13. A one-piece dental implant according to claim 12, wherein the constricted zone is approximately one-third of the length of the post.

14. A one-piece dental implant according to claim 1, wherein the dental implant is made of a material selected from the group consisting of titanium and titanium with 15% molybdenum.

15. A one-piece dental implant according to claim 14, wherein the titanium used in the dental implant has a tensile strength in the range of approximately 250–450 MPa.

16. A one-piece dental implant according to claim 1, wherein the hardness of the material used to make the implant is a function of the forces expected to be transferred by the dental implant and a geometric configuration of the dental implant.

17. A one-piece dental implant according to claim 1, wherein the foot part further includes a guide bevel.

18. A one-piece dental implant according to claim 1, wherein the post includes a basal part and wherein the surfaces of the foot part and the basal part of the post are enlarged.

19. A one-piece dental implant according to claim 1, wherein the post includes a crestal part having a smooth surface and wherein the crestal part of the post is oriented in the vicinity of a mucosa region and a crestal part of the jaw upon insertion of the implant into the jaw.

20. A one-piece dental implant according to claim 1, wherein the bar has a round profile cross-section.

21. A one-piece dental implant according to claim 1, wherein the bar has an oval profile cross-section.

22. A one-piece dental implant according to claim 1, further including a second, basal foot part and a shaft connecting the foot part and the second, basal foot part and wherein the surfaces of the post and the foot part are smooth and the surfaces of the second, basal foot part and the shaft are enlarged.

23. A one-piece dental implant according to claim 1, further including at least a second bar and a third bar wherein said bars extend radially from said post, said bars being at substantially equidistant radial angles from each other and wherein the frame includes first and second segments that join the ends of the bars.

24. The one piece dental implant according to claim 23 further comprising a fourth bar, each of said bars extending radially from said post and each of said bars being substantially equidistant at substantially equidistant radial angles from each other.

25. The one piece dental implant according claim 24 wherein each of said bars are about 90 degrees from each other.

26. The one piece dental implant according to claim 24 further comprising a first segment of said geometric form, said segment being substantially curvilinear and said segment extending between a distal end of said first bar and a distal end of said second bar;
 a second segment of said geometric form, said second segment extending from a distal end of said third bar to a distal of said fourth bar, and said second segment being generally rectilinear in shape.

27. A one-piece dental implant according to claim 1, wherein a connection of the bar with the post includes a first transition radius and a second transition radius.

28. A one-piece dental implant according to claim 1, wherein the connection between the post and the bar includes a transition radius and wherein the transition radius extends over an angle of greater than about 90°.

29. A one-piece dental implant according to claim 1, wherein the dental implant is made of an alloy including titanium and molybdenum.

30. The one piece dental implant according to claim 1 wherein a portion of said geometric form is curvilinear in shape and said curvilinear portion has a radius centered upon said post, said radius being approximately one half of an overall width of said geometric form.

31. A one-piece dental implant adapted for endosteal and combined endosteal/subperiosteal osseointegration in a jaw, including:
 first and second force-transferring foot parts for insertion into a jaw, each foot part including a frame in a closed geometric form having an interior open area and at least one bar connected with the frame and extending into the interior open area of the geometric form, said geometric form including at least a partial ring shape; each of said foot parts, frame and bars being substantially on a single plane, said plane of said first foot part being substantially parallel to said plane of said second foot part,
 a post connecting the first foot part with the second foot part, wherein the first and second foot parts have a distance greater than about 3 mm between them; and
 said post being adapted to projects out of the jaw, said post being connected with the first foot part through the bar of the first foot part and said post being connected with the second foot part through the bar of the second foot part.

* * * * *